US010806753B2

(12) United States Patent
Ohno et al.

(10) Patent No.: US 10,806,753 B2
(45) Date of Patent: Oct. 20, 2020

(54) CORE-SHELL CROSSLINKED HYALURONIC ACID GEL PARTICLES, PRODUCTION METHOD FOR SAME, AND MEDICAL MATERIAL

(71) Applicant: DENKA COMPANY LIMITED, Tokyo (JP)

(72) Inventors: Akio Ohno, Tokyo (JP); Masamichi Hashimoto, Tokyo (JP); Harei Nemoto, Tokyo (JP); Takafumi Harada, Tokyo (JP); Kenji Fujii, Tokyo (JP)

(73) Assignee: Denka Company Limited, Tokyo (JP)

( * ) Notice: Subject to any disclaimer, the term of this patent is extended or adjusted under 35 U.S.C. 154(b) by 48 days.

(21) Appl. No.: 16/050,269

(22) Filed: Jul. 31, 2018

(65) Prior Publication Data

US 2018/0333430 A1 Nov. 22, 2018

Related U.S. Application Data

(62) Division of application No. 14/903,199, filed as application No. PCT/JP2014/068195 on Jul. 8, 2014, now abandoned.

(30) Foreign Application Priority Data

Jul. 8, 2013 (JP) ................. 2013-142828

(51) Int. Cl.
*A61K 31/728* (2006.01)
*C08B 37/08* (2006.01)
*A61K 9/00* (2006.01)
*A61L 26/00* (2006.01)
*A61L 15/28* (2006.01)
*A61L 27/20* (2006.01)
*A61K 9/50* (2006.01)
*A61L 31/04* (2006.01)
*A61K 9/48* (2006.01)

(52) U.S. Cl.
CPC .......... *A61K 31/728* (2013.01); *A61K 9/0019* (2013.01); *A61K 9/4816* (2013.01); *A61K 9/5036* (2013.01); *A61L 15/28* (2013.01); *A61L 26/0023* (2013.01); *A61L 27/20* (2013.01); *A61L 31/042* (2013.01); *C08B 37/0072* (2013.01); *A61L 2400/04* (2013.01); *A61L 2400/06* (2013.01); *A61L 2430/24* (2013.01); *A61L 2430/34* (2013.01)

(58) Field of Classification Search
None
See application file for complete search history.

(56) References Cited

U.S. PATENT DOCUMENTS 5,885,609 A * 3/1999 Amiji ............... A61L 33/0076
424/425
9,216,193 B2 12/2015 Hashimoto et al.

2006/0188966 A1 8/2006 DeAngelis
2008/0193536 A1 8/2008 Khademhosseini et al.
2010/0028437 A1* 2/2010 Lebreton ............... A61L 27/52
424/488
2013/0203697 A1* 8/2013 Hashimoto .......... C08B 37/0072
514/54

FOREIGN PATENT DOCUMENTS

| CN | 1326352 A | 12/2001 | | |
|---|---|---|---|---|
| CN | 1342171 A | 3/2002 | | |
| CN | 101573123 A | 11/2009 | | |
| CN | 102548590 A | 7/2012 | | |
| CN | 103124558 A | 5/2013 | | |
| EP | 2011816 A1 | 1/2009 | | |
| JP | 2004-181121 A | 7/2004 | | |
| JP | 2012-041512 A | 3/2012 | | |
| WO | WO 2008/147817 A2 | 12/2008 | | |
| WO | WO 2012/026468 A1 | 3/2012 | | |
| WO | WO-2012026468 A1 * | 3/2012 | ............ | A61Q 19/08 |
| WO | WO 2013/089888 A2 | 9/2013 | | |

OTHER PUBLICATIONS

Kablik, Jeffrey et al.; "Comparative Physical Properties of Hyaluronic Acid Dermal Fillers," 2009, Wiley; Dermatologic Surgery, vol. 35, pp. 302-312. (Year: 2009).*
Fakhari et al.; "Applications and emerging trends of hyaluronic acid in tissue engineering, as dermal filler and in osteoarthritis treatment," 2013; Elsevier; Acta Biomaterialia, vol. 9, pp. 7081-7092. (Year: 2013).*
Tezel; "The Science of hyaluronic acid dermal fillers," 2008, Infoma; Journal of Cosmetic and Laser Therapy, vol. 10, pp. 35-42). (Year: 2008).*
Fernandes et al., "Swelling and mechanical properties of polymer gels with cross-linking gradient," *The Royal Society of Chemistry, Soft Matter*, 6: 3455-3458 (2010).
Jia et al., "Hyaluronic Acid-Based Microgel Networks for Vocal Fold Regeneration," *American Chemical Society, Biomacromolecules*, 7: 3336-3344 (2006).
Kupal et al., "Biointerface properties of Core-Shell Poly(vinyl alcohol)-hyaluronic Acid Microgels Based on Chemoselective Chemistry," *American Chemical Society, Biomacromolecules*, 13: 3592-3601 (2012).
Schiavinato et al., "Comparison of the effects of intra-articular injections of Hyaluronan and its chemically cross-linked derivative (Hylan G-F20) in normal rabbit knee joints", *Clinical and Experimental Rheumatology*, vol. 20, pp. 445-454 (2002).

(Continued)

*Primary Examiner* — Devang K Thakor
*Assistant Examiner* — Ivan A Greene
(74) *Attorney, Agent, or Firm* — Leydig, Voit & Mayer, Ltd.

(57) ABSTRACT

A core-shell gel particle of the invention contains a crosslinked hyaluronic acid, has a higher equilibrium swelling capacity at the surface than at the center, the equilibrium swelling capacity showing a change curve with an inflection point from the center to the surface, and has a probe pushing force of 20 nN or less from the surface to a depth of 800 nm.

4 Claims, 4 Drawing Sheets

(56) References Cited

OTHER PUBLICATIONS

Wu, "Study on Hyaluronic Acid Solutions and Freeze-Thaw Gels", A Dissertation Submitted to Shanghai Jiao Tong University for the Degree of Master/ China Master's Theses Full-Text Database, *Engineering Science*, vol. 1, No. 7 (2012).
European Patent Office, Extended European Search Report issued in European Patent Application No. 14822114.6 (dated Feb. 9, 2017) 8 pages.
International Preliminary Report on Patentability, dated Jan. 21, 2016, in International Application No. PCT/JP2014/068195.
International Search Report, dated Sep. 22, 2014, in International Application No. PCT/JP2014/068195.

* cited by examiner

CORE-SHELL CROSSLINKED HYALURONIC ACID GEL PARTICLES, PRODUCTION METHOD FOR SAME, AND MEDICAL MATERIAL

CROSS-REFERENCE TO RELATED APPLICATIONS

This application is a divisional of U.S. Patent Application Ser. No. 14/903,199, filed on Jan. 6, 2016, which is the U.S. National Phase Application of International Application No. PCT/JP2014/068195, filed Jul. 8, 2014, claiming priority from Japanese Application No. 2013-142828, filed Jul. 8, 2013, the disclosures of each of which are incorporated herein by reference in their entireties for all purposes.

TECHNICAL FIELD

The present invention relates to a core-shell crosslinked hyaluronic acid gel particle, a manufacturing thereof and a medical material.

BACKGROUND ART

Hyaluronic acid is a linear macromolecular polysaccharide comprising β-D-N-acetylglucosamine and β-D-glucuronic acid in alternating linkage. Because hyaluronic acid exhibits excellent biocompatibility and viscoelasticity, it is becoming ever more widely used in the medical field. For example, various types of solution preparations are being marketed as viscosity replenishers for gonarthrosis.

Hyaluronic acid is widely distributed in vertebrate vitreous bodies, joint fluids, skin and elsewhere, and is commonly used in pharmaceuticals including suborbital surgical adjuvants and intraarticular infusions, as well as in medical equipment, cosmetics and health foods. Since hyaluronic acid, as an intrinsic biological component, is present at high concentrations in tissues and organs, it is fundamentally highly safe.

Crosslinked hyaluronic acid gels are also known as hyaluronic acid. For example, a viscosity replenisher using self-crosslinked hyaluronic acid particles is disclosed in Patent Literature 1, which teaches that the drug effect is increased by gelation of hyaluronic acid to a high concentration.

Various crosslinked hyaluronic acid gels with increased bioretention are also being marketed (for example, Synvisc™, Durolane™, Monovisc™ and Gel-One™).

However, while crosslinked hyaluronic acid gels have the feature of improved bioretention, they are known to cause a weak foreign body reaction, unlike hyaluronic acid solutions (Non-Patent Literature 1).

CITATION LIST

Patent Literature

[Patent Literature 1] International Patent Publication No. WO12/026468

Non-Patent Literature

[Non-Patent Literature 1] Clin. Exp. Rheumatol., Vol. 20, p. 445-454 (2002)

SUMMARY OF INVENTION

Technical Problem

It is an object of the present invention to provide a crosslinked hyaluronic acid gel particle with high biocompatibility, where the foreign body reaction is reduced to a level comparable to hyaluronic acid solutions.

It is another object of the invention to provide a method for manufacturing the gel particle and a medical material including the gel particle.

Solution to Problem

The invention provides a core-shell gel particle comprising a crosslinked hyaluronic acid (core-shell crosslinked hyaluronic acid gel particle), the particle having a higher equilibrium swelling capacity at the surface than at the center, the equilibrium swelling capacity showing a change curve with an inflection point from the center and the surface, and the particle having a probe pushing force of 20 nN or less from the surface to a depth of 800 nm.

The core-shell crosslinked hyaluronic acid gel particle of the invention has a surface with a degree of softness similar to a hyaluronic acid solution, and despite having virtually the same molecular structure, the particle reduces foreign body reactions and exhibits high biocompatibility.

The core-shell gel particle preferably has the equilibrium swelling capacity of 40 or greater from the inflection point to the surface. In other words, in a change curve of the equilibrium swelling capacity, obtained by plotting the length of the core-shell crosslinked hyaluronic acid gel particle from the center of gravity in the surface direction on the abscissa (X), and the equilibrium swelling capacity at a prescribed abscissa position on the ordinate (Y), the value (Y) of the equilibrium swelling capacity is preferably 40 or greater between the abscissa position ($X_c$) where the inflection point exists to the abscissa position ($X_s$) corresponding to the surface.

If the equilibrium swelling capacity around the surface of the core-shell crosslinked hyaluronic acid gel particle is within this range, then it is possible to ensure that the particle surface has softness even closer to that of a hyaluronic acid solution, and therefore the core-shell crosslinked hyaluronic acid gel particle has foreign body reactions reduced to about the same level as a hyaluronic acid solution, and exhibits high biocompatibility.

The invention also provides a core-shell gel particle comprising a crosslinked hyaluronic acid, the particle having a higher equilibrium swelling capacity at the surface than at the center, the equilibrium swelling capacity showing a change curve with an inflection point from the center to the surface, and the particle having the equilibrium to swelling capacity of 65 or greater from the inflection point to the surface.

The core-shell crosslinked hyaluronic acid gel particle has a surface with a degree of softness similar to a hyaluronic acid solution, and despite having virtually the same molecular structure, the particle reduces foreign body reactions and exhibits high biocompatibility.

In the core-shell crosslinked hyaluronic acid gel particle, a distance from the inflection point to the surface is preferably 5 μm or greater. That is, the length from the abscissa position ($X_c$) to the abscissa position ($X_s$) is preferably 5 μm or greater in the core-shell crosslinked hyaluronic acid gel particle.

Since the distance from the inflection point to the surface is within this range, it is possible to ensure the thickness of the soft section of the particle surface, and even if the surface decomposes in the joints or elsewhere after the particle has been administered, a surface with a high equilibrium swelling capacity is newly exposed from the interior, and foreign body reactions are reduced to about the same level as a hyaluronic acid solution while high biocompatibility is retained, over prolonged periods.

The present invention also provides a method for manufacturing the above core-shell gel particle, the method comprising the step of contacting a gel particle containing a crosslinked hyaluronic acid with a basic substance to form a core-shell structure in the gel particle.

Since the Core-shell crosslinked hyaluronic acid gel particle obtained by this method has surface with softness close to that of a hyaluronic acid solution, and is not readily recognized as crosslinked hyaluronic acid gel particle in the body, the particle has foreign body reactions reduced to about the same level as a hyaluronic acid solution, and exhibits high biocompatibility.

The invention still further provides a method for manufacturing the core-shell gel particle, the method comprising the step of forming a shell of a crosslinked hyaluronic acid gel on the surface of a gel particle containing a crosslinked hyaluronic acid, the crosslinked hyaluronic acid gel having a lower crosslink density of hyaluronic acid than the gel particle.

Since the core-shell crosslinked hyaluronic acid gel particle obtained by this method also has surface with softness close to that of a hyaluronic acid solution, and is not readily recognized as crosslinked hyaluronic acid gel particles in the body, the particle has foreign body reactions reduced to about the same level as a hyaluronic acid solution, and exhibits high biocompatibility.

The invention still further provides a medical material comprising the above core-shell gel particle.

The medical material including such a core-shell crosslinked hyaluronic acid gel particle is not readily recognized as foreign matter in the body, and is therefore resistant to inflammation reactions even when the medical material is administered into the body, and it is possible to ensure high biocompatibility similar to medical materials comprising hyaluronic acid solutions.

The medical material can be used as any one selected from intraarticular infusions, pharmacologically active substance supports, wound coverings, tissue-replacing biological tissue repair agents, antiadhesive agents, hemostatic agents, artificial extracellular matrices and dermal fillers.

Since such a medical material is not readily recognized as foreign matter in the body and is therefore resistant to inflammation reactions, it is possible to ensure high biocompatibility similar to medical materials containing hyaluronic acid solutions. In light of the above, the medical material is more preferably used as an intraarticular infusion.

Advantageous Effects of Invention

According to the invention it is possible to provide crosslinked hyaluronic acid gel particle with high biocompatibility, where foreign body reactions are reduced to a level comparable to hyaluronic acid solutions.

It is also possible to provide a method for manufacturing the gel particle and a medical material including the gel particle.

DESCRIPTION OF EMBODIMENTS

Figure 1:
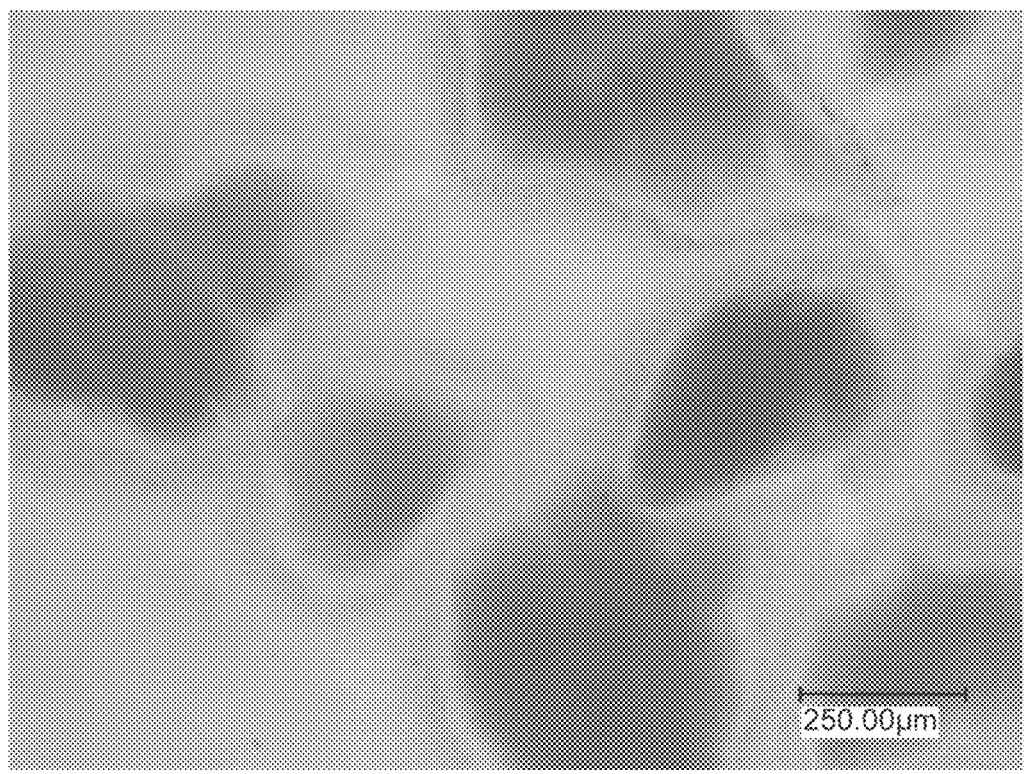
FIG. 1 is a photomicrograph of core-shell crosslinked hyaluronic acid gel particles according to an embodiment of the invention, negatively stained with an aqueous nigrosine solution after methylene blue staining.

Preferred embodiments of the invention is described below, with the understanding that these embodiments are in no way limitative on the invention.

The core-shell gel particle(s) containing a crosslinked hyaluronic acid (core-shell crosslinked hyaluronic acid gel particle(s)) is explained first. The core-shell crosslinked hyaluronic acid gel particles of this embodiment are particles wherein the equilibrium swelling capacity shows a change curve with an inflection point from the center to the surface. The core-shell crosslinked hyaluronic acid gel particles need only have particle-like forms in the gel state, and do not necessarily need to be spherical. Also, the "center" of a core-shell crosslinked hyaluronic acid gel particle is the center of gravity of the particle, and the location can be identified using a microscope image or the like. The phrase "the equilibrium swelling capacity shows a change curve with an inflection point from the center to the surface" means that an inflection point is present on the change curve obtained by plotting the equilibrium swelling capacity, with the equilibrium swelling capacity on the ordinate and the linear distance from the center toward the particle surface on the abscissa (the center being abscissa 0). The plot is preferably every 0.2 to 15 μm on the abscissa (preferably every 0.5 to 5 μm on the abscissa), and the change curve is preferably obtained as a fitted curve of the plot.

The change curve may have multiple inflection points, but it preferably has only a single inflection point. The shape of the change curve is preferably such that the equilibrium swelling capacity curve rises sharply in a specific region of the abscissa (The equilibrium swelling capacity preferably changes gradually before and after rising. That is, it preferably has a single inflection point, the rate of change of the slope of the change curve preferably changing from positive to negative before and after the inflection point), with the inflection point being present within the specific region. Also, the particle portion inside of the inflection point may be referred to as the "core", and the particle portion outside of the inflection point may be referred to as the "shell". Several straight lines may be imagined from the center to the surface of the core-shell crosslinked hyaluronic acid gel particles, but one of the straight lines is selected as the abscissa, with the equilibrium swelling capacity changing as described above.

The equilibrium swelling capacity of the crosslinked hyaluronic acid gel particles can be calculated by confocal laser Raman spectroscopy. Using confocal laser Raman spectroscopy, the hyaluronic acid concentration may be analyzed within a specified minute range of the gel particles, and by using a sample with known equilibrium swelling capacity as reference, the equilibrium swelling capacity in the specified minute range can be calculated. Also, since the equilibrium swelling capacity can be calculated for any specified minute range within the gel particles, repeating calculation of the equilibrium swelling capacity by confocal laser Raman spectroscopy, and shifting the specified minute range, allows behavioral changes in the equilibrium swelling capacity in the gel particles to be observed.

The measurement is divided into two stages. The first stage is a stage in which a value correlated with hyaluronic acid concentration is calculated, based on the ratio between the peak Raman intensity attributable to water, obtained by analyzing a specified minute range within the gel particles that are in an equilibrium swelled state in an aqueous solvent (buffering solution), and the peak Raman intensity attributable to hyaluronic acid. The second stage is a stage in which a sample with known equilibrium swelling capacity is used to create a calibration curve for numerical values correlating between equilibrium swelling capacity and hyaluronic acid concentration, and the equilibrium swelling capacity is calculated based on the value correlating with the hyaluronic acid concentration in the specified minute range within the crosslinked hyaluronic acid gel particles. More specifically, a measuring section is designated in a range of 0.5 to 5 μm in the crosslinked hyaluronic acid gel particles, based on an optical microscope image, the Raman intensity ratio is determined for the wavenumber attributable to C—H bonds of hyaluronic acid (2940 cm$^{-1}$) with respect to the wavenumber attributable to O—H bonds (3420 cm$^{-1}$) based on the obtained spectrograph, and calculation is performed by the following formula (1).

Calculated equilibrium swelling capacity=[($H_{O-H}$/$H_{C-H}$)−intercept of calibration curve]/slope of calibration curve (1)

($H_{O-H}$: 3420 cm$^{-1}$ Raman intensity, $H_{C-H}$: 2940 cm$^{-1}$ Raman intensity)

The equilibrium swelling capacity of the crosslinked hyaluronic acid gel particles overall is expressed as the ratio of the volume of the gel particles that have been removed out by filtration of the gel particles that are in the equilibrium swelled state in an aqueous solvent (buffering solution), and the volume when the gel particles have been further dried.

The equilibrium swelling capacity can be calculated by the following formula (2), using the ratio (Qw) of the wet weight of the crosslinked hyaluronic acid gel when the aqueous solvent (buffering solution) has been removed by filtration, and the weight of the dried crosslinked hyaluronic acid gel, and the density.

Equilibrium swelling capacity=1+(ρ/ρ0)×(Qw−1) (2)

(ρ: Density of crosslinked hyaluronic acid gel particles, ρ0: density of aqueous solvent (buffering solution))

There are no particular restrictions on the method of removing the aqueous solvent (buffering solution) by filtration, and for example, centrifugal filtration using a centrifugal filter unit, vacuum filtration using a membrane filter, or the like, may be applied as appropriate.

Since the equilibrium swelling capacity is affected by the salt concentration of the solvent, as well as the pH, temperature, swelling time, etc., the measurement is performed in 10 mM phosphate-buffered saline (pH 6.0), with a NaCl concentration of 0.9 wt % and swelling at 5° C. for 1 day, after an equilibrium swelled state has been reached.

Depending on the composition of the core-shell crosslinked hyaluronic acid gel particles and the method of measuring the equilibrium swelling capacity, the equilibrium swelling capacity at the inflection point may be in the range of 20 to 80 (especially in the range of 40 to 60, or about 50).

For core-shell crosslinked hyaluronic acid gel particles, the probe pushing force from the surface to a depth of 800 nm is 20 nN or less. The depthwise direction referred to here is preferably the direction from the surface toward the center (center of gravity). Also, the probe pushing force is measured as the elasticity which is measured using a scanning probe microscope. Specifically, the crosslinked hyaluronic acid gel particles in an equilibrium swelled state in an aqueous solvent (buffering solution) are placed on a sample stage, and a colloidal probe having a 10 μm-diameter (spherical) glass bead mounted on the tip is pushed upward from the surface of the crosslinked hyaluronic acid gel to a depth of 800 nm, while measuring the force on the probe (probe pushing force).

The pushing force is preferably 10 nN or less. A pushing force of 20 nN or less corresponds to low elasticity of the surfaces of the core-shell crosslinked hyaluronic acid gel particles, so that they are not readily recognized as foreign matter in the body, thereby reducing inflammation reactions, even when they have been administered into the body, and it is possible to ensure high biocompatibility similar to a hyaluronic acid solution.

The equilibrium swelling capacity of the region from the inflection point to the surface, i.e. the shell, is preferably 40 or greater, more preferably 50 or greater and even more preferably 65 or greater. If the equilibrium swelling capacity of the shells of the core-shell crosslinked hyaluronic acid gel particles is within this range, then it is possible to ensure that the particle surfaces have softness similar to that of a hyaluronic acid solution, so that it is possible to obtain particles that are not readily recognized as foreign matter in the body, have foreign body reactions reduced to about the same level as a hyaluronic acid solution, and exhibit high biocompatibility. From the viewpoint described above, the equilibrium swelling capacity is most preferably 75 or greater. The equilibrium swelling capacity of the shell is a higher value than the equilibrium swelling capacity at the aforementioned inflection point.

The distance from the inflection point to the surface in the thickness direction of the core-shell crosslinked hyaluronic acid gel particles is preferably 5 μm or greater. This distance may be the moving distance from the inflection point to a point on the surface, when the equilibrium swelling capacity in a specified minute range from the center toward the surface is successively measured for one or more locations of the core-shell crosslinked hyaluronic acid gel particles. If the shell thickness is within this range, the core-shell crosslinked hyaluronic acid gel particles are not readily recognized as foreign matter in the body, and it is possible to ensure high biocompatibility similar to a hyaluronic acid solution. Also, since decomposition of the shell surface sections having a high equilibrium swelling capacity, after the gel particles have been administered intraarticularly, for example, produces new shell surface sections with a high equilibrium swelling capacity from the interiors, it is possible to maintain long-term high biocompatibility similar to a hyaluronic acid solution. From the viewpoint described above, the thickness of the shells is more preferably 10 μm or greater.

The thickness of the shell of a core-shell crosslinked hyaluronic acid gel particle can be measured as the length in the thickness direction of the transparent section of the outer shell, based on microscopic observation of a core-shell crosslinked hyaluronic acid gel particle that has been stained only in the core. Specifically, an image of the stained core-shell crosslinked hyaluronic acid gel is observed with a digital microscope, and the distance from the gel particle surface to the border between the core and the shell is measured at one or more points for each gel particle. The measurement is performed for 100 gel particles, and the shell thickness can be calculated from the average value.

The staining may be carried out by any known method that allows staining of hyaluronic acid, but staining by methylene blue or acridine orange is preferred. Also, it is more preferred to negatively stain the aqueous solvent alone with nigrosine or the like, in order to facilitate distinction of the border between the transparent shell and aqueous solvent. Specifically, the core-shell crosslinked hyaluronic acid gel particles that are in an equilibrium swelled state in the aqueous solvent (buffering solution) are stained by adding an aqueous solution of methylene blue and thoroughly stirring. Next, the sample may be s placed on a sample stage and subjected to negative staining by addition of an aqueous nigrosine solution just before observation with a digital microscope.

A method of manufacturing core-shell crosslinked hyaluronic acid gel particles is described below.

According to an embodiment of the invention, the source of the hyaluronic acid used is not restricted, and it may be extracted from animal tissue or produced by a fermentation method.

The strain used for the fermentation method is preferably a microorganism having hyaluronic acid manufacturing ability, such as *Streptococcus* isolated from the natural world, or a variant that produces stable hyaluronic acid at a high yield, such as *Streptococcus equi* FM-100 (FERM P-9027) described in Japanese Unexamined Patent Application Publication No. S63-123392 or *Streptococcus equi* FM-300 (FERM P-2319) described in Japanese Unexamined Patent Application Publication No. H2-234689.

The hyaluronic acid can be used in the form of a salt that is acceptable for the technical field, such as a sodium, potassium or lithium salt.

The crosslinked hyaluronic acid gel particles used may be self-crosslinked hyaluronic acid gel particles having an ester structure as the self-crosslinking of the hyaluronic acid.

The self-crosslinked hyaluronic acid gel particles are obtained by combining hyaluronic acid, water at 5 mass % or greater of the hyaluronic acid concentration, and an acid component in at least an equimolar amount as the carboxyl groups of the hyaluronic acid, and maintaining their combined state at low temperature.

The acid to be combined with the hyaluronic acid is not particularly restricted, and any known acid may be used, although it is preferably a stronger acid than hyaluronic acid, and more preferably an inorganic acid. More preferably, it is hydrochloric acid, nitric acid or sulfuric acid, among which nitric acid is particularly preferred, having excellent handling properties. The amount of acid to be combined is not particularly restricted, and the amount of acid component is at least an equimolar amount as the carboxyl groups of the hyaluronic acid. The acid to be combined with the hyaluronic acid is preferably kept in is an amount such that it is present at 15 mass % or greater, preferably 20 mass % or greater and 40 mass % or less of the total hyaluronic acid. It may be kept at a temperature of between −30° C. and 25° C., for any period of from 1 hour to 20 days. Most preferably, it is kept at a temperature of between −25° C. and −5° C. for 1 to 15 days. Mixture of the hyaluronic acid with the acid to be combined with the hyaluronic acid is preferably carried out by adding the hyaluronic acid with the acid to be combined, to 15 mass % or greater and preferably 20 mass % or greater of the total, forming a uniform state of the acid to be combined. In addition, it may be impregnated to 15 mass % or greater and preferably 20 mass % or greater of the total acid to be combined with the hyaluronic acid, or an acidic aqueous solution of hyaluronic acid adjusted to a low concentration may be concentrated so that the hyaluronic acid is at 15 mass % or greater and preferably 20 mass % or greater of the total.

The concentration of the obtained self-crosslinked hyaluronic acid gel particles in the suspension may be quantified in the following manner for example. First, the self-crosslinked hyaluronic acid gel suspension is diluted with distilled water, a sodium hydroxide aqueous solution is added and the mixture is allowed to stand at room temperature, for hydrolysis of the ester bonds of the self-crosslinked hyaluronic acid gel particles to cause dissolution. Next, hydrochloric acid was added to the solution for neutralization, and then the glucuronic acid concentration was quantified by the carbazole-sulfuric acid method, known to those skilled in the art. The glucuronic acid concentration and a known concentration of hyaluronic acid may be used as standard substances to calculate the concentration of self-crosslinked hyaluronic acid gel particles in the suspension.

The method for manufacturing the core-shell crosslinked hyaluronic acid gel particles may be a surface treatment method in which a portion of the crosslinked structure of the surface section of the crosslinked hyaluronic acid gel particles is degraded to soften it into a shell, or a shell synthesis method in which a soft shell is formed on the surfaces of the particles. Core-shell crosslinked hyaluronic acid gel particles obtained by such a manufacturing method is not readily recognized as foreign matter in the body, and therefore can minimize inflammation reactions and can ensure high bio compatibility similar to a hyaluronic acid solution.

The surface treatment method may be a method in which portions of the crosslinked surface sections of the crosslinked hyaluronic acid gel particles are broken up by chemical treatment capable of specifically degrading the crosslinked structure of hyaluronic acid, lowering the crosslink density of the hyaluronic acid to increase the equilibrium swelling capacity, or in other words, to produce a softer shell. This allows a core-shell structure to be formed on the crosslinked hyaluronic acid gel particles. Any combination may be employed for the hyaluronic acid crosslinked structure and the chemical treatment that can specifically degrade it, and for example, it may be a combination of the ester structure which is the self-crosslinking of the hyaluronic acid, and treatment with a basic substance, The method for manufacturing core-shell crosslinked hyaluronic acid gel particles by this combination is a method in which the self-crosslinked hyaluronic acid gel particles are used as starting material and swelled with an acidic solution, after which the gel particle surfaces are contacted with the basic substance in a liquid mixture of water and a water-soluble organic solvent. As the basic substance permeates from the surface to the interior of the self-crosslinked hyaluronic acid gel particles, it degrades the ester bonds, increasing the equilibrium swelling capacity at the permeated sections.

The acidic solution used to swell the self-crosslinked hyaluronic acid gel particles is not particularly restricted, and any known acid may be used, although it is preferably a water-soluble acid, and more preferably a strong inorganic acid. Also, the concentration of the acidic solution is not particularly restricted, but preferably it is a concentration that is at least equimolar with respect to the carboxyl groups of the self-crosslinked hyaluronic acid gel particles. The amount of the acidic solution is also not particularly restricted, and for example, it is preferably a 0.1 to 20-fold molar amount and more preferably a 0.3 to 5-fold molar amount with respect to the carboxyl groups of the self-crosslinked hyaluronic acid gel particles.

The water-soluble organic solvent of the liquid mixture is not particularly restricted, and any publicly known water-soluble organic solvent may be used, but it is preferably glycerin, dimethyl sulfoxide, ethanol, methanol, ethylene glycol or polyethylene glycol, and most preferably glycerin.

The proportion of the water-soluble organic solvent in the liquid mixture is not particularly restricted but is preferably 50% or greater, more preferably 60 to 90% and most preferably 70 to 80%.

The basic substance is not particularly restricted and may be any publicly known basic substance, but it is preferably a basic substance that dissolves in the mixture of water and a water-soluble organic solvent, and more preferably quaternary ammonium hydroxide. Such a basic substance is more preferably hexadecyltrimethylammonium hydroxide, dimethyldistearylammonium hydroxide or tetrabutylammonium hydroxide, and most preferably hexadecyltrimethylammonium hydroxide, which is amphiphilic. The amount of the basic substance is not particularly restricted, but it is preferably a 1- to 30-fold molar amount, and more preferably a 2 to 10-fold molar amount, of the acidic solution used to swell the self-crosslinked hyaluronic acid gel particles.

The shell synthesis method described above is a method in which a shell of a crosslinked hyaluronic acid gel with lower crosslink density of hyaluronic acid than the crosslinked hyaluronic acid gel particles, is formed on the surfaces of the crosslinked hyaluronic acid gel particles. The method of synthesizing the shell to be formed is not particularly restricted, and core-shell crosslinked hyaluronic acid gel particles can be produced by any publicly known method for synthesizing a crosslinked hyaluronic acid gel.

Specifically, the hyaluronic acid solution, a compound with crosslinking groups, and a crosslinking agent are mixed in the presence of the crosslinked hyaluronic acid gel particles, or a hyaluronic acid solution modified with crosslinking groups and a crosslinking agent are mixed in the presence of the crosslinked hyaluronic acid gel particles, to faun a shell of a crosslinked hyaluronic acid gel with a lower crosslink density of hyaluronic acid than the crosslinked hyaluronic acid gel particles, on the surfaces of the gel particles.

There are no particular restrictions on the solution dissolving the hyaluronic acid or the hyaluronic acid modified with crosslinking groups, but a liquid mixture of water and a water-soluble organic solvent is preferred, in which case the water-soluble organic solvent is most preferably THF, dioxane, acetone, ethanol or the like.

Hyaluronic acid modified with crosslinking groups is modified hyaluronic acid having a structure wherein one of the crosslinking groups having a structure with the ability to bind with hyaluronic acid at both ends, is bonded with the hyaluronic acid, and it is modified hyaluronic acid having the ability to gel by a crosslinking agent alone, without addition of a compound with crosslinking groups.

The compound with crosslinking groups is not particularly restricted, and may be a compound having any publicly known crosslinking groups that can crosslink hyaluronic acid, but it is preferably a compound that allows crosslinking reaction to take place under mild neutral reaction conditions.

The crosslinking agent is not particularly restricted, and may any publicly known crosslinking agent capable of crosslinking hyaluronic acid, but it is preferably a crosslinking agent that can promote crosslinking reaction under mild neutral reaction conditions.

The core-shell crosslinked hyaluronic acid gel particles may be used in any general field using medical materials and hyaluronic acid, without any particular restrictions, and examples include use in intraarticular infusions, pharmacologically active substance supports, wound coverings, tissue-replacing biological tissue repair agents, antiadhesive agents, hemostatic agents, artificial extracellular matrices, dermal fillers, or other biomedical products such as medical equipment or medical tools, or medical compositions used for diagnosis or therapy. Among these, a particularly notable effect is exhibited when they are used as an intraarticular infusion.

Core-shell crosslinked hyaluronic acid gel particles are not readily recognized as foreign matter in the body, allowing inflammation reactions to be minimized and ensuring high biocompatibility similar to a hyaluronic acid solution. The high biocompatibility of the core-shell crosslinked hyaluronic acid gel particles according to the embodiment of the invention, more specifically, is such that when analysis is conducted using as the index the increasing leukocyte count due to local stimulation by the gel particle in rabbit knee joints, the leukocyte count does not exceed $100 \times 10^4$/mL, and more preferably the leukocyte count does not exceed $10 \times 10^4$/mL, in 6 mL of a collected knee joint synovial fluid sample dilution.

EXAMPLES

The invention is described in greater detail by examples, with the understanding that the invention is not limited thereto.

Comparative Example 1

After placing 75 g of 2N nitric acid in a rotating and revolving kneader (product of Primix Corp.), it was cooled to −10° C. to obtain sherbet-like frozen nitric acid, Into the frozen nitric acid there was loaded 22.5 g of sodium hyaluronate powder with a viscosity-average molecular weight of 2,200,000 (moisture content: 10%), and the mixture was kneaded at −10° C., 100 rpm for 1 hour, to a uniform rubber-like consistency (sodium hyaluronate: 20.8 mass %). The obtained mixture of hyaluronic acid and nitric acid was stored for 10 days in a freezer set to −20° C. The mixture was then loaded into 1 L of purified water at 5° C., and the purified water was exchanged twice every hour. The mixture was then further loaded into 1 L of 50 mM phosphate buffer at 5° C., the 50 mM phosphate buffer was exchanged 5 times every hour, and neutralized rinsing was conducted until the nitric acid completely disappeared, to obtain an self-crosslinked hyaluronic acid gel.

The obtained self-crosslinked hyaluronic acid gel was allowed to stand for 30 minutes after neutralization, the supernatant was removed by decantation, and a 9-fold weight of 50 mM phosphate buffer was added to the precipitated self-crosslinked hyaluronic acid gel. The self-crosslinked hyaluronic acid gel suspension was loaded into a high-speed rotation device and fragmented, to obtain a suspension of self-crosslinked hyaluronic acid gel particles.

The suspension of the self-crosslinked hyaluronic acid gel particles was allowed to stand for 30 minutes, and the supernatant was removed by decantation. To the remaining suspension of self-crosslinked hyaluronic acid gel particles there was added a 9-fold weight of physiological saline, exchanging the physiological saline 10 times every 10 minutes. Next, it was sorted with a sieve in order of largest aperture (testing sieve: lead-free, diameter: 150 mm, depth: 60 mm, apertures: 500 µm, 355 µm, 212 µm, 125 µm, 53 µm), and there were obtained six self-crosslinked hyaluronic acid gel particle suspensions with different particle diameters (>500 µm, 500 to 355 µm, 355 to 212 µm, 212 to 125 µm, 125 to 53 µm, <53 µm).

The obtained self-crosslinked hyaluronic acid gel particle suspensions were rinsed width distilled water and ethanol and dried under reduced pressure to obtain dried self-crosslinked hyaluronic acid gel particles.

The equilibrium swelling capacity of the self-crosslinked hyaluronic acid gel particles was calculated in the following manner. A 0.4 ml suspension of the self-crosslinked hyaluronic acid gel particles (solvent: 10 mM phosphate-buffered saline (pH 6.0), sodium chloride concentration: 0.9 wt %) was subjected to centrifugal separation at 5° C., 2000 rpm for 30 minutes using a centrifugal filter unit (0.45 micrometer pore size, product of Millipore) to remove the solvent, and the weight of the solvent-removed self-crosslinked hyaluronic acid gel particles was measured. The particles were s further dried for 20 hours, and the weight of the dried self-crosslinked hyaluronic acid gel particles was measured. Upon calculating the equilibrium swelling capacity based on both measured values, the equilibrium swelling capacity of the obtained self-crosslinked hyaluronic acid gel particles was found to be 5.9.

Example 1

The dried self-crosslinked hyaluronic acid gel particles obtained in Comparative Example 1 (0.1 g, 500 to 355 µm) were swelled for 3 minutes in 0.5 M hydrochloric acid (0.7 mL) at room temperature (20 to 25° C.). A liquid mixture of a 25% hexadecyltrimethylammonium hydroxide/methanol solution (1.65 mL) and 80% aqueous glycerin (45 mL) was added, and after stirring for 8 minutes, 6 M hydrochloric acid (0.5 mL) was added for neutralization.

Rinsing was performed 5 times each with 70% ethanol and physiological saline, and core-shell crosslinked hyaluronic acid gel particles were obtained as a physiological saline suspension.

The yield of the obtained core-shell crosslinked hyaluronic acid gel particles was determined as follows. The total amount of supernatant of the obtained core-shell crosslinked hyaluronic acid gel particle suspension was removed, and dilution was performed with distilled water. There was added 1N sodium hydroxide (2 mL), stirring was performed for 2 minutes for dissolution, and 1N hydrochloric acid (2 mL) was added for neutralization. The hyaluronic acid concentration of the obtained hyaluronic acid solution was calculated by the carbazole-sulfuric acid method, and the yield was calculated from the amount of the hyaluronic acid solution and the amount of the starting self-crosslinked hyaluronic acid gel particles, and found to be 92%.

Example 2

Core-shell crosslinked hyaluronic acid gel particles were obtained by the same method as Example 1, except that the aqueous 80% glycerin solution was changed to an aqueous 80% dimethyl sulfoxide solution, and the stirring time was changed from 8 minutes to 3 minutes. The yield was 82%.

Example 3

Core-shell crosslinked hyaluronic acid gel particles were obtained by the same method as Example 1, except that the aqueous 80% glycerin solution was changed to an aqueous 70% ethanol solution, and the stirring time was changed from 8 minutes to 3 minutes. The yield was 61%.

Example 4

Core-shell crosslinked hyaluronic acid gel particles were obtained by the same method as Example 3, except that the 0.5 M hydrochloric acid was changed to 0.5 M acetic acid. The yield was 3%.

Example 5

Core-shell crosslinked hyaluronic acid gel particles were obtained by the same method as Example 1, except that the stirring time was changed from 8 minutes to 12 minutes. The yield was 89%.

Example 6

Core-shell crosslinked hyaluronic acid gel particles were obtained by the same method as Example 3, except that the 25% hexadecyltrimethylammonium hydroxide/methanol solution was changed to a 25% dimethyldistearylammonium hydroxide/methanol solution. The yield was 77%.

Comparative Example 2

Core-shell crosslinked hyaluronic acid gel particles were obtained by the same method as Example 3, except that the aqueous 70% ethanol solution was changed to an aqueous 10% ethanol solution. The yield was 54%.

Comparative Example 3

Core-shell crosslinked hyaluronic acid gel particles were obtained by the same method as Example 3, except that swelling with 0.5 M hydrochloric acid was not carried out. The yield was 70%.

Reference Example 1

The hyaluronic acid articular formulation "Suvenyl" (trade name of Chugai Pharmaceutical Co.; viscosity-average molecular weight: 2,000,000, hyaluronic acid concentration: 1 w/v %) was used.

Test Example 1

The elasticity on the surfaces of the core-shell crosslinked hyaluronic acid gel particles of Examples 1 to 6 and Comparative Examples 2 to 3 was analyzed based on probe pushing force on the surface, using a scanning probe microscope. The measuring conditions were as follows.
Scanning probe microscope: Model SPM-9700 (trade name of Shimadzu Corp.)
Probe: Colloidal probe equipped with 10 µm-diameter (spherical) glass bead (CP-CONT-BSG-B, product of Toyo Technica)
Pushing distance: 800 nm
Times measured: 3
Measuring temperature: 23±2° C.

A physiological saline suspension of each of the crosslinked hyaluronic acid gel particles was sampled onto a sample mount in the device, and set on the device stage. While observing the crosslinked hyaluronic acid gel particles with an optical microscope, the probe was set above the measuring position and a force curve was obtained while moving the probe directly downward about 3000 nm. Using the force curve obtained from the measurement, the slack distance of the probe from the particle surface to a pushing distance of 800 nm was multiplied by the spring constant of the probe, to calculate the size of the force and obtain the elasticity.

Test Example 2

The equilibrium swelling capacity for the core-shell crosslinked hyaluronic acid gel particles of Examples 1 to 6 and Comparative Examples 2 to 3 was analyzed based as the calculated value corresponding to the equilibrium swelling capacity of the crosslinked hyaluronic acid gel particles using a confocal laser Raman spectroscope with hyaluronic acid concentration as the reference.

Each physiological saline suspension of crosslinked hyaluronic acid gel particles was sampled onto slide glass, and the suspension surface was covered with cover glass for use as the measuring sample. The sample was placed on a XYZ 3-axis automatic stage in the confocal laser Raman spectroscope, and an optical microscope was used to set the observation origin near the exterior of a crosslinked hyaluronic acid gel particle. Using the automatic measuring function, which involves repeated linear movement in the horizontal direction and vertical direction toward the center of gravity of the particle, and measurement, the Raman spectrum was successively obtained within a minute range of 0.5 to 5 μm. The measuring conditions were as follows.
Confocal laser Raman spectroscope: Almega-XR (trade name of Thermo Fisher Scientific, KK.)
Laser wavelength: 532 nm
Exposure time: 1.0 seconds
Exposures: 8
Measurement wavenumber: 4232 to 116 cm$^{-1}$
Measuring temperature: 25±2° C.

Based on the Raman spectrum, formula (3) shown below was used to calculate the equilibrium swelling capacity in a minute range of 0.5 to 5 μm, The measured values for the equilibrium swelling capacity were successively plotted, a fitted curve was obtained from a sigmoid function, the average value from the location of the inflection point on the fitted curve, i.e. the border between the core and shell, to the surface (which can also be judged as the point where the equilibrium swelling capacity calculated from the Raman spectrum begins to undergo large variation (noise), and the moving average value of the equilibrium swelling capacity becomes constant) was calculated as the equilibrium swelling capacity of the shell.

$$\text{Calculated equilibrium swelling capacity} = [(H_{O-H}/H_{C-H}) - 3.1598]/0.2947 \quad (3)$$

($H_{O-H}$: 3420 cm$^{-1}$ Raman intensity, $H_{C-H}$: 2940 cm$^{-1}$ Raman intensity)

Figure 4:
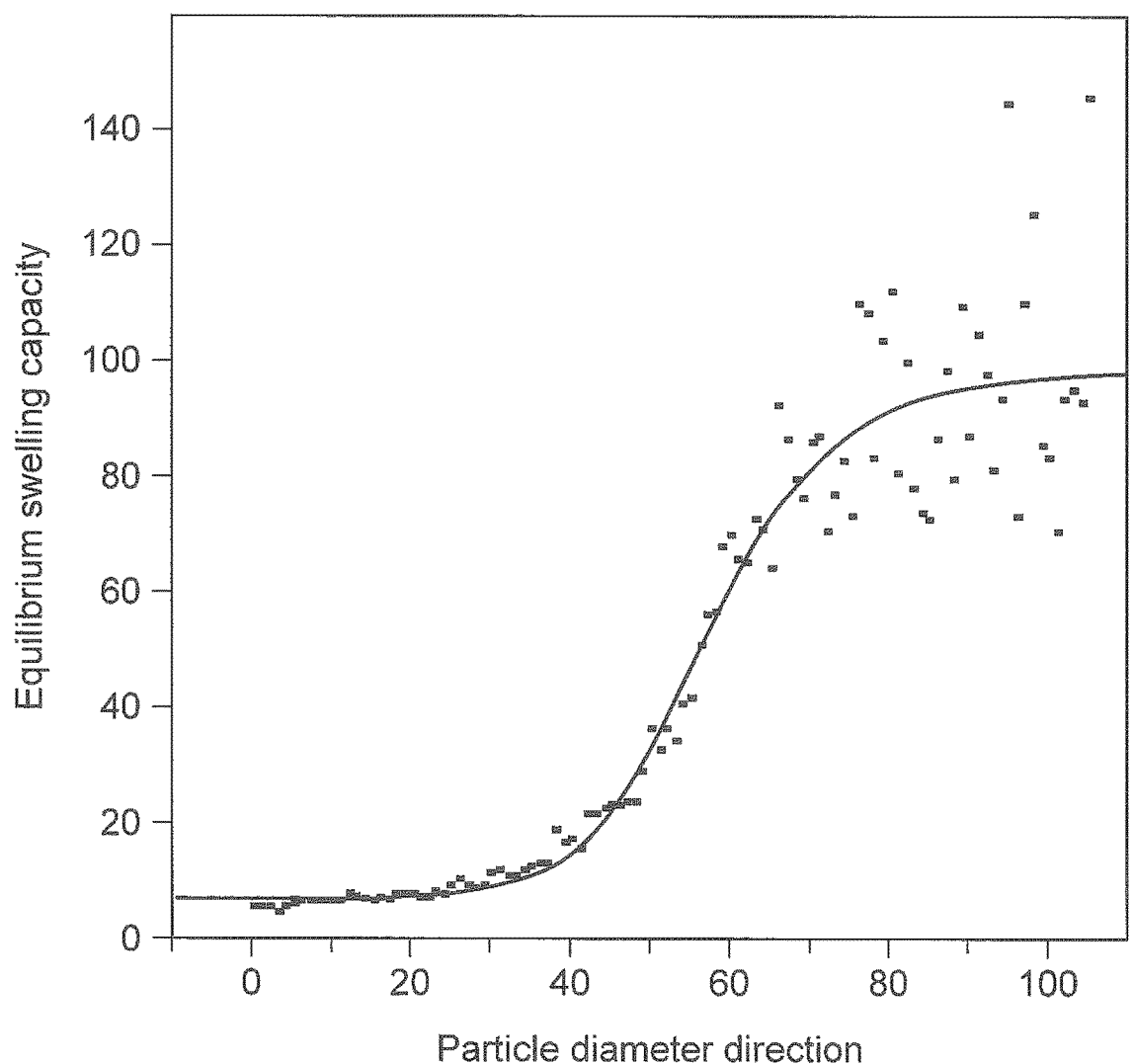
FIG. 4 is a graph showing a change curve of the equilibrium swelling capacity of core-shell crosslinked hyaluronic acid gel particles according to an embodiment of the invention.

From the plot of the equilibrium swelling capacity, a fitted curve was obtained from a sigmoid function, and this was used as the change curve for the equilibrium swelling capacity. A graph of the obtained change curve is shown in FIG. 4. The inflection point was determined for the change curve. Judgment was also made by the method described above for the surface location.

In addition, when judgment of the border between the shell and exterior was difficult, the physiological saline was removed from the sample and it was instead suspended in a water-insoluble liquid (for example, a hydrocarbon compound such as paraffin) having no peak at a wavenumber of (3420 cm$^{-1}$) due to O—H bonds of water, thereby increasing variation in the calculated values for the equilibrium swelling capacity of the shell and exterior for calculation of the equilibrium swelling capacity.

Test Example 3

A 5 μL portion of a 1% water-soluble methylene blue solution was added to 500 μL of a physiological saline suspension of the core-shell crosslinked hyaluronic acid gel particles of Examples 1 to 6 and Comparative Examples 2 to 3 and of the self-crosslinked hyaluronic acid gel particles of Comparative Example 1. After standing at room temperature for 15 minutes or longer, 70 μL was sampled onto slide glass, 1 μL of a 1% aqueous nigrosine solution was further added, and a digital microscope (VHX-500F, trade name of Keyence Corp.) was used to take a microscope image of the crosslinked hyaluronic acid gel particles. The obtained image is shown in FIG. 1.

Based on the obtained microscope image, the border of staining with methylene blue was determined to be the border between the core and shell while the border of staining with nigrosine was determined to be the border between the shell and physiological saline, and the thickness of the shell at one location per particle was measured. The average value of the thicknesses of a total of 100 gel particle shells was calculated, and that value was recorded as the shell thickness.

In the method described above, the 1% aqueous methylene blue solution was also changed to a 1% aqueous acridine orange hydrochloride solution, and the shell thickness was calculated in the same manner.

Test Example 4

The equilibrium swelling capacity was calculated in the same manner as Test Example 2 for the core-shell crosslinked hyaluronic acid gel particles of Examples 1 to 6 and Comparative Examples 2 to 3 and the self-crosslinked hyaluronic acid gel particles of Comparative Example 1, and the analyzed moving distance from the border between the core and shell to the border between the shell surface and the exterior physiological saline was calculated as the shell thickness.

Test Example 5

In order to evaluate the tissue affinity of the core-shell crosslinked hyaluronic acid gel particles of Examples 1 to 6 and Comparative Examples 2 to 3, the self-crosslinked hyaluronic acid gel particles of Comparative Example 1 and the hyaluronic acid solution of Reference Example 1, analysis was performed using increased leukocyte count upon local stimulation with each sample in rabbit knee joints as the index.

Adjustment of the composition containing the core-shell crosslinked hyaluronic acid gel particles for injection for evaluation in the animals was conducted in the following manner.

The core-shell crosslinked hyaluronic acid gel particle suspensions obtained in Examples 1 to 6 and Comparative Examples 2 to 3 were adjusted in the following manner to a dry weight (concentration) of 3 w/v % of the crosslinked hyaluronic acid gel particles with respect to the total volume.

Quantification of the concentration of the core-shell crosslinked hyaluronic acid gel particles was accomplished by diluting 50 mg of sample in 1.55 ml of distilled water, adding 0.2 ml of a 1N sodium hydroxide solution and allowing the mixture to stand at room temperature for 30 minutes for hydrolysis of the ester crosslinks of the core-shell crosslinked hyaluronic acid gel particles, and dissolution of the core-shell crosslinked hyaluronic acid gel particles. Also, 0.2 ml of 1N hydrochloric acid was added for neutralization, and then the carbazole-sulfuric acid method was used to calculate the core-shell crosslinked hyaluronic acid gel particle concentration, with a known concentration of hyaluronic acid (viscosity-average molecular weight: 1,900,000) as the standard substance. Based on these quantified results, the concentration of the core-shell crosslinked hyaluronic acid gel particles was adjusted to 3 w/v %, and a core-shell crosslinked hyaluronic acid gel particle composition for evaluation in animals was obtained.

Adjustment of the composition containing the self-crosslinked hyaluronic acid gel particles for injection for evaluation in animals was conducted in the following manner.

A suspension of the self-crosslinked hyaluronic acid gel particles obtained in Comparative Example 1 was poured into 10 mM phosphate-buffered saline at 5° C., pH 7.0, exchanging the 10 mM phosphate-buffered saline each hour, and this was repeated twice. The following method was carried out, similar to quantification of the core-shell crosslinked hyaluronic acid gel particle concentration described above, so that the dry weight (concentration) of the self-crosslinked hyaluronic acid gel particles was 3 w/v % with respect to the total volume of the crosslinked hyaluronic acid composition.

After allowing it to stand for a conditioning period of 1 day or longer, 0.1 mL/kg of the injection of Examples 1 to 6 or Comparative Examples 2 to 3 was administered into the intraarticular cavity of one knee and 0.1 mL/kg of the injection of Comparative Example 1 or Reference Example 1 was administered into the intraarticular cavity of the other knee, using a 1 mL glass syringe (1 mL Terumo syringe for tuberculin, product of Terumo Corp.) and a 20 or 21G injection needle (20G or 21G Terumo injection needle, product of Terumo Corp.). The administered liquid volume was calculated separately by calculating the liquid volume based on body weight as measured on the day of administration.

One day after administration, the rabbits were slaughtered by fatal bloodletting for collection of the knee synovial fluid. Physiological saline was then injected into the intraarticular cavity using a 1 mL glass syringe and 18G injection needle. After sufficiently moving the knee joint, a 1 mL glass syringe and 18G injection needle were used to collect the knee synovial fluid. This procedure was repeated 4 times to obtain approximately 2 mL of knee synovial fluid sample.

The collected knee synovial fluid sample was diluted 3-fold with physiological saline, thoroughly shaken and uniformly suspended, after which 100 µL was sampled, and 2 µL of staining solution (LABOSTAIN, trade name of Muto Pure Chemicals Co., Ltd.) was added to stain the leukocytes. A 15 µL portion of the stained synovial fluid was sampled in a Neubauer hemocytometer and a microscope was used to determine the leukocyte count within a 1×1×0.1 mm region. The average value for 4 chambers was recorded as the leukocyte count for each knee joint, and the leukocyte count for each injection, as an index of the biocompatibility, was determined as the average leukocyte count for 3 or more knee joints.

As shown in Table 1, the core-shell crosslinked hyaluronic acid gel particles of Examples 1 to 6 had improved biocompatibility compared to the self-crosslinked hyaluronic acid gel particles of Comparative Example 1 and the core-shell crosslinked hyaluronic acid gel particles of Comparative Examples 2 to 3, and similar to the hyaluronic acid solution of Reference Example 1. This demonstrated that the presence or absence of shells on gel particles, and the thickness and softness of the shells, are important for biocompatibility.

TABLE 1

|  | Shell softness | | Shell thickness (µm) | | Biocompatibility | |
| --- | --- | --- | --- | --- | --- | --- |
|  | Elasticity/ nN | Equilibrium swelling capacity | Staining | Analyzed moving distance of equilibrium swelling capacity | Leukocyte count (×10$^4$/mL) | Remark |
| Example 1 | 7.8 | 76 | 10 | 10 | 10 | Core-shell |
| Example 2 | 5.2 | 91 | 23 | 18 | 4 | crosslinked |
| Example 3 | 3.5 | 79 | 42 | 38 | 2 | hyaluronic |
| Example 4 | 3.0 | 79 | 88 | 89 | 13 | acid gel |
| Example 5 | 8.1 | 78 | 15 | 15 | 13 | particles |
| Example 6 | 4.9 | 94 | 30 | 28 | 9 |  |
| Comp. Example 1 | — | — | 0 | 0 | 210 | Self-crosslinked hyaluronic acid gel particles |
| Comp. Example 2 | 48 | 58 | 44 | 38 | 203 | Core-shell crosslinked |
| Comp. Example 3 | 35 | 63 | 30 | 28 | 146 | hyaluronic acid gel particles with hard shell |
| Reference Example 1 | — | — | — | — | 9 | Hyaluronic acid solution |

Test Example 6

The effects of intraarticular cavity injection of the core-shell crosslinked hyaluronic acid gel particles of Examples 3 to 4 and the hyaluronic acid solution of Reference Example 1 on pain were confirmed using an experimental arthrosis deformans animal model, with rabbit knee joint meniscus excision.

The animals prepared were 13-week-old Kbl:JW (SPF) rabbits (male), and as conditioning for the evaluating device, a procedure was conducted in which they were introduced into the main container (holder) of a small animal pain-evaluating Incapacitance Tester (trade name of Linton Instruments), and rendered immobile for 5 seconds.

The animals were separately housed in a bracket type metal wire mesh cage (350 W×500 D×350 Hmm) equipped with an adjustable rack, and raised in an environment of 25±3° C. temperature, 50±20% humidity, 12-18 air ventilations/hour, and an illumination time of 8:00 to 20:00 (12 hours of light, 12 hours of darkness). The sample was administered as restricted feeding with 150 g/day of RC4 experimental animal solid feed (product of Oriental Yeast Co., Ltd.) using a stainless steel feeder, and drinking water was freely provided as tap water through a polypropylene water supply bottle (stainless steel tube end). The individual animals were distinguished by writing individual identification numbers on the ears with a magic marker, and before division into groups in the cages, cards were assigned bearing their gender and individual identification number, while after division into groups, cards were assigned bearing their test number, administration group, gender, animal number, day of excision, day of administration, day of examination and individual identification number.

Division into groups was on the day prior to meniscus excision. On the day of division into groups, the body weight and weight distribution of both hind legs of all the animals were measured. The left hind leg weight distribution ratio (left load/total load on both sides)×100(%)) was calculated from the measured weight distribution of both hind legs. Based on the left hind leg weight distribution ratio, individuals were selected in order of proximity of their individual value to the average value. The selected animals were divided into groups using a stratified continuous randomization method based on the left hind leg weight distribution ratio. After confirming that the average value for the left hind leg weight distribution ratio was the same for each group, with no differences between the groups, it was confirmed that the average body weight was also the same value for each group, with no differences between the groups.

The meniscus excision was conducted on the day following division into groups, with the day of meniscus excision being defined as postoperative day 0. Using 14- to 15-week-old animals, an animal model with arthrosis deformans of meniscus excision was prepared, referring to the methods described in References 1 to 3.

For example, Reference 1 describes preparation of 32 KBL:JW rabbits (13-week-old, female), cutting out of the outer collateral ligament and sesamoid ligament of the left knee joint under ketamine and xylazine anesthesia, partial excision of 3.0 to 4.0 mm of the meniscus, using a 26G injection needle for injection of high molecular weight HA solution for 8 each in groups A and B and injection of physiological saline for 8 in the control group C, into the knee joint at a frequency of 5 times during a 2-week period, oral administration of Loxonin each day to group C and group D, and evaluation of the pain-relieving effect and cartilage deformation-preventing effect. Also, Reference 2 describes preparation of 72 New Zealand white rabbits (2 to 3 kg body weight), amputation of the left knee joint ligament under anesthesia, partial excision of 3 to 4 mm of the meniscus, injection of 1 to 0.01% HA solution with a molecular weight of 1,900,000 for 48 in group A, injection of 1 to 0.01% HA solution with a molecular weight of 800,000 for 12 in group B and injection of physiological saline for 12 in group C, into the knee joint at a frequency of twice per week for a period of 2 and 4 weeks, and after slaughtering, sampling of the knee joints and evaluation of the drug effect. In addition, Reference 3 describes preparation of 15 Japan white rabbits (female, 2.5 kg), amputation of the outer collateral ligament and sesamoid ligament of the left knee joint under pentobarbital sodium anesthesia, partial excision of 3.0 to 4.0 mm of the meniscus, using a 25G injection needle for injection into the knee joint at a frequency of twice per week, injection of the same amount of physiological saline as a control, and after slaughtering, sampling of the knee joints and evaluation of the drug effect.

Reference 1: Osteoarthritis and Cartilage, Vol. 15, No. 5, p. 543-549 (2007)
Reference 2: Osteoarthritis and Cartilage, Vol. 4, No. 2, p. 99-110 (1996)
Reference 3: Kansetsu Geka, Vol. 15, No. 3, p. 92-98 (1996)
Reference 4: Yakuri to Chiryo, Vol. 23, p. 833-841 (1995)
Reference 5: Yakuri to Chiryo, Vol. 33, p. 303-312 (2005)
Reference 6: Seikeigeka Kiso Kagaku, Vol. 9, p. 77-79 (1982)
Reference 7: Seikeigeka Kiso Kagaku, Vol. 11, p. 125-127 (1984)
Reference 8: Arthritis & Rheumatism, Vol. 48, No. 7, p. 1923-1929 (2003)

The left knee joints of the rabbits were shaved under combined anesthesia with ketamine hydrochloride (Ketalar for intramuscular injection, 500 mg, product name of Sankyo Yell Yakuhin Co., Ltd.) and xylazine (Skilpe 2% injection, product name of Intervet, K.K.) by intramuscular injection into the femoral region, and anchored in the supine position on a Kitajima brace (product of Natsume Seisakusho Co., Ltd.). After aseptically creating an approximately 2-cm incision in the skin directly below the outer side of the patella to expose the outer collateral ligament, the ligament was excised. Also, the tendon in the politeal muscle origin was excised to expose the outer meniscus, and approximately the center section of the meniscus was excised across a 3.0 to 4.0 mm region. Next, the subcutaneous tunica muscularis and skin were each sutured with a knotted suture and the femoral region was intramuscularly injected with approximately 0.2 mL of ampicillin (Viccilin Sol-15%, product name of Meiji Seika Kaisha, Ltd.).

On postoperative day 4 (day of pain onset), after measurement of the weight distribution of both hind legs, 0.1 mL/kg of the injections of Examples 3 to 4 and Reference Example 1 was administered once into the surgically operated (left) intraarticular cavity using a 1 mL glass syringe and a 23G injection needle. The administered liquid volume was calculated separately by calculating the liquid volume based on the body weight as measured on the day of administration.

For measurement of the weight distribution of both hind legs there was used a pain evaluating Incapacitance Tester for small animals. The testing device precisely detected the weight distribution on the left and right legs of the animal placed in the main container with a dual channel sensor pad set on the container bottom, with the left and right weights in gram units, and the value was averaged over a time set by the experimenter. The main container used was one designed for rabbits. The set measuring time was 5 seconds, with the animal in an immobile state.

The animal was transferred to the main container (holder) for rabbits, the immobile state of the animal was measured (first time), after which the animal was removed from the holder, reinserted, and measured in an immobile state (second time), and the procedure was repeated (third time). For each third measurement of the weight distribution of both hind legs, the left hind leg weight distribution ratio (%) was calculated from the left and right weights (loads), by the following formula (4).

Left hind leg weight distribution ratio (%)={Left load (g)/(right load (g)+left load (g))×100}      (4)

The average value for the third calculated left hind leg weight distribution ratio (%) was defined as the left hind leg weight distribution ratio (%) for each measurement. The results are shown in FIG. 2 and FIG. 3.

Figure 2:
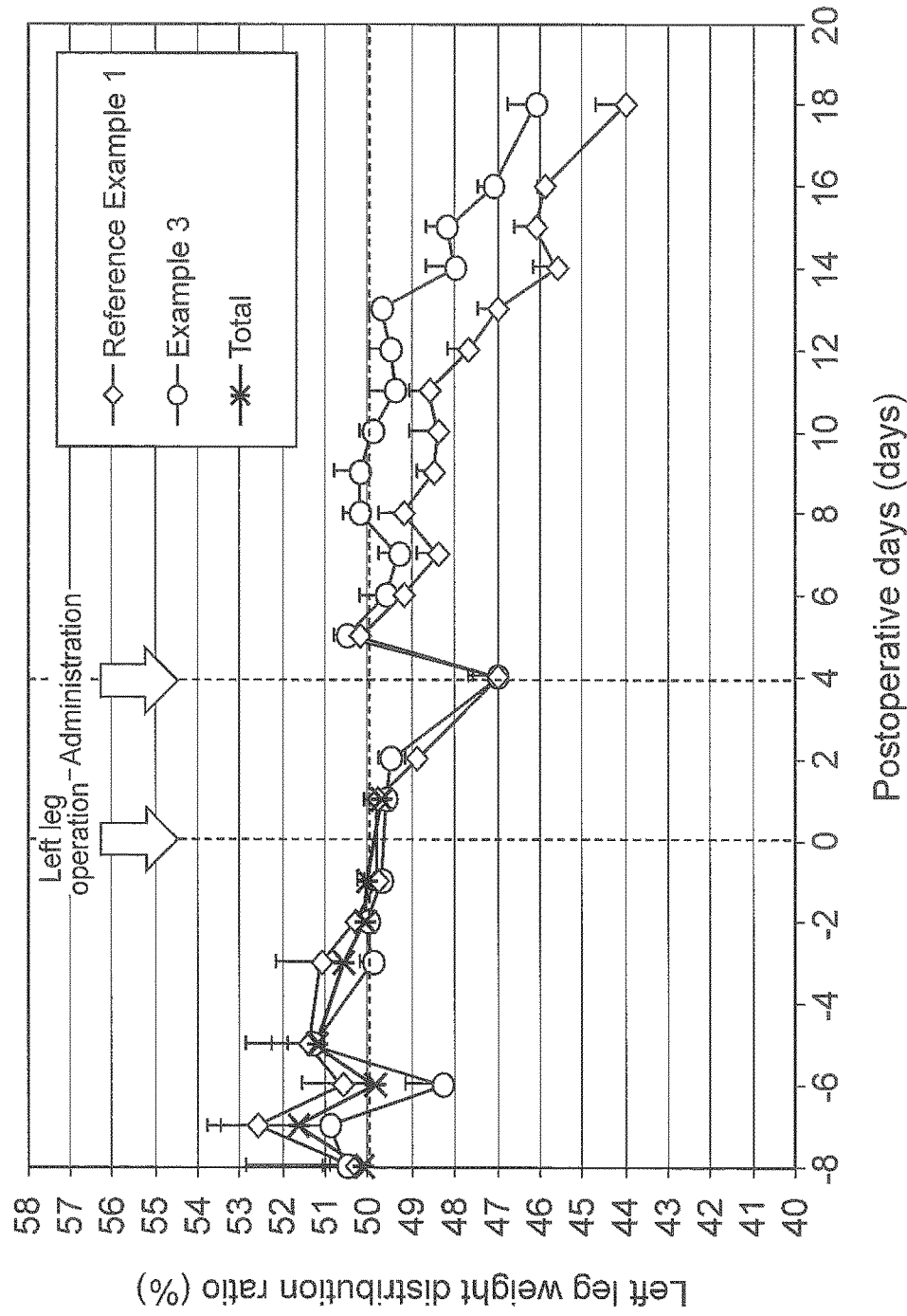
FIG. 2 is a graph showing a comparison of the pain-relieving effects of an intraarticular infusion comprising core-shell crosslinked hyaluronic acid gel particles according to an embodiment of the invention, and a hyaluronic acid formulation.
Figure 3:
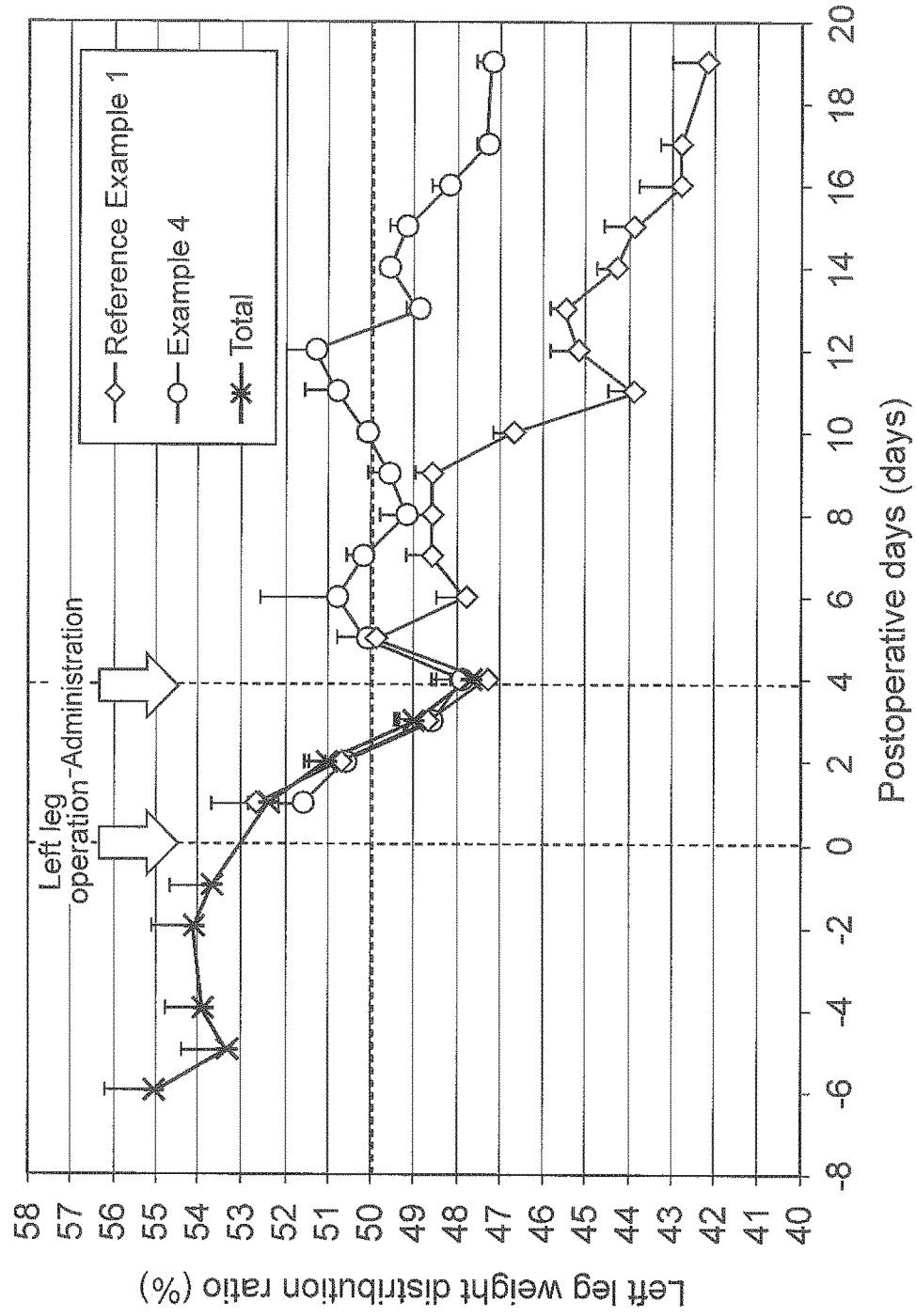
FIG. 3 is a graph showing a comparison of the pain-relieving effects of an intraarticular infusion comprising core-shell crosslinked hyaluronic acid gel particles according to an embodiment of the invention, and a hyaluronic acid formulation.

As shown in FIG. 2 and FIG. 3, the rabbits administered the core-shell crosslinked hyaluronic acid gels of Examples 3 to 4 maintained a pain-relieving effect longer than the rabbits administered the hyaluronic acid solution of Reference Example 1.

INDUSTRIAL APPLICABILITY

According to the invention it is possible to provide core-shell crosslinked hyaluronic acid gel particles with high biocompatibility, where the foreign body reaction is reduced to a level comparable to a hyaluronic acid solution. It is also possible to provide a method for manufacturing the gel particles and a medical material including the gel particles.

The invention claimed is:

1. A method for manufacturing a core-shell gel particle comprising a crosslinked hyaluronic acid,
the method comprising the step of utilizing a gel particle containing a self-crosslinked hyaluronic acid as starting material and swelling the gel particle with an acidic solution, and contacting the resulting gel particle with a basic substance in a liquid mixture of water and a water-soluble organic solvent to form a core-shell structure in the gel particle,
wherein the proportion of the water-soluble organic solvent in the liquid mixture is 50% or greater,
wherein the core-shell gel particle has a higher equilibrium swelling capacity at the surface than at the center, the equilibrium swelling capacity showing a change curve with an inflection point from the center to the surface, wherein the change curve is obtained by plotting the length of the core-shell crosslinked hyaluronic acid gel particle from the center of gravity in the surface direction on the abscissa (X) and the equilibrium swelling at a prescribed abscissa position on the ordinate (Y), and the particle having a probe pushing force of 20 nN or less from the surface to a depth of 800 nm.

2. The method for manufacturing the core-shell gel particle according to claim 1, wherein the equilibrium swelling capacity is 40 or greater from the inflection point to the surface.

3. A method for manufacturing a core-shell gel particle comprising a crosslinked hyaluronic acid,
the method comprising the step of utilizing a gel particle containing a self-crosslinked hyaluronic acid as starting material and swelling the gel particle with an acidic solution, and contacting the resulting gel particle with a basic substance in a liquid mixture of water and a water-soluble organic solvent to form a core-shell structure in the gel particle,
wherein the proportion of the water-soluble organic solvent in the liquid mixture is 50% or greater,
wherein the core-shell gel particle has a higher equilibrium swelling capacity at the surface than at the center, the equilibrium swelling capacity showing a change curve with an inflection point from the center to the surface, wherein the change curve is obtained by plotting the length of the core-shell crosslinked hyaluronic acid gel particle from the center of gravity in the surface direction on the abscissa (X) and the equilibrium swelling at a prescribed abscissa position on the ordinate (Y), and the particle having a equilibrium swelling capacity of 65 or greater from the inflection point to the surface.

4. The method for manufacturing the core-shell gel particle according to claim 1, wherein a distance from the inflection point to the surface is 5 μm or greater.

* * * * *